(12) United States Patent
Stough

(10) Patent No.: US 7,056,324 B2
(45) Date of Patent: Jun. 6, 2006

(54) WART REMOVAL METHOD AND DEVICE

(76) Inventor: Dowling B. Stough, 3633 Central Ave., Suite I, Hot Springs, AR (US) 71913

( * ) Notice: Subject to any disclaimer, the term of this patent is extended or adjusted under 35 U.S.C. 154(b) by 332 days.

(21) Appl. No.: 10/610,366

(22) Filed: Jun. 30, 2003

(65) Prior Publication Data

US 2004/0138679 A1    Jul. 15, 2004

Related U.S. Application Data

(63) Continuation-in-part of application No. 09/851,477, filed on May 8, 2001, now Pat. No. 6,585,742.

(51) Int. Cl.
*A61B 17/50*    (2006.01)
(52) U.S. Cl. ...................... 606/131; 604/500
(58) Field of Classification Search ............... 604/500, 604/46–48, 289, 131; 132/137, 76.4
See application file for complete search history.

(56) References Cited

U.S. PATENT DOCUMENTS 5,997,549 A * 12/1999 Sauceda et al. ............. 606/131

* cited by examiner

*Primary Examiner*—(Jackie) Tan-Uyen T. Ho
(74) *Attorney, Agent, or Firm*—Speed Law Firm; Gary N. Speed; Kyla D. Cummings

(57) ABSTRACT

A wart removal device is disclosed. The device has a handle and first and second pluralities of tines having different heights. One set of tines has a height of approximately 0.04 inch or less, and the other set has a height of approximately 0.08 inch or less. The different sets may be disposed on opposite sides of the handle at the same end of the handle or may be disposed on opposite ends of the handle. In operation, the longer set of tines is raked against wart tissue to create a plurality of incisions in the wart tissue. This treatment is repeated over a time period. After that time period, the shorter set of tines is used. The tines create incisions without causing noticeable bleeding. The device may be used in combination with a medicament and may be provided as a kit, including the device and a medicament.

12 Claims, 5 Drawing Sheets

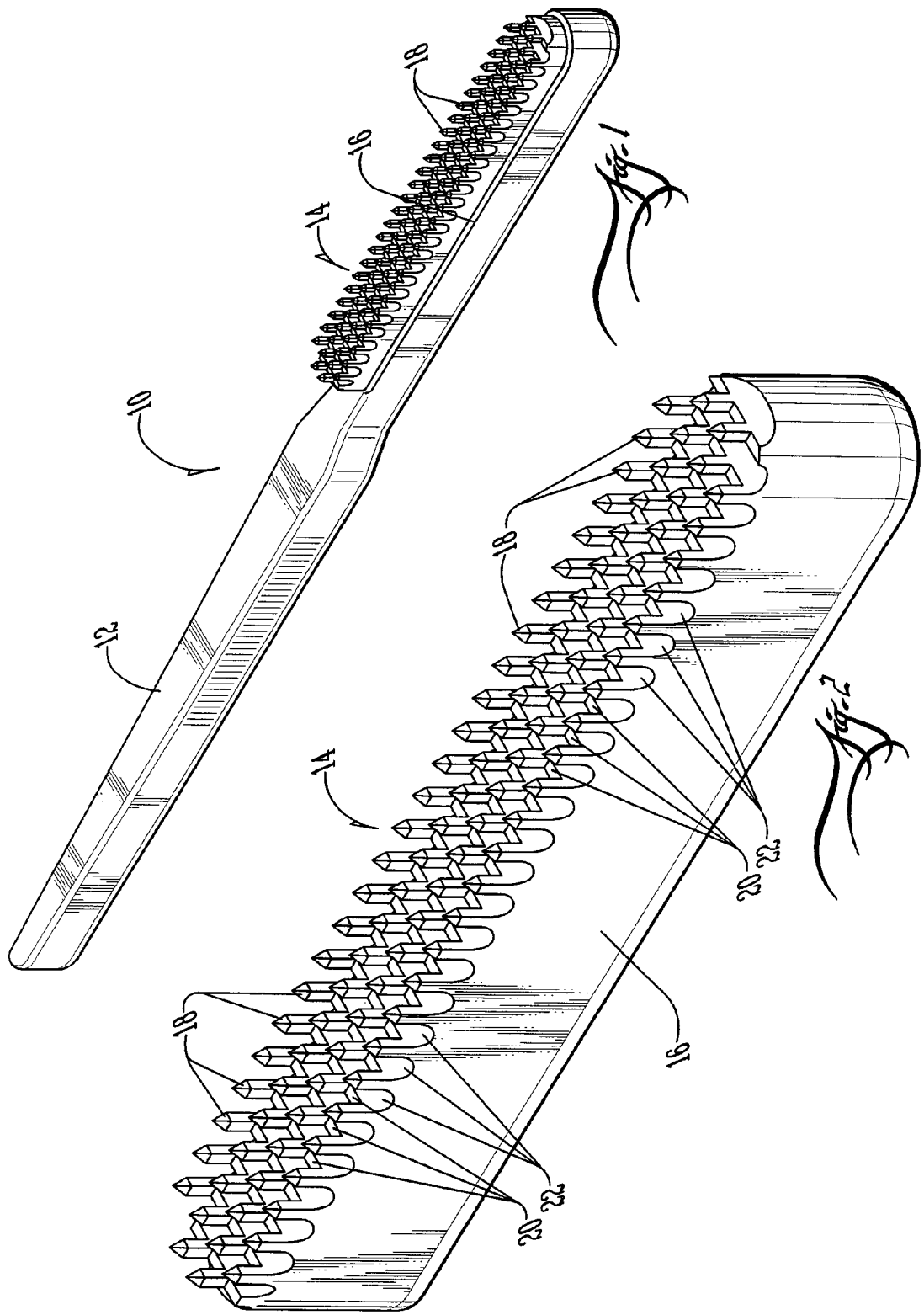

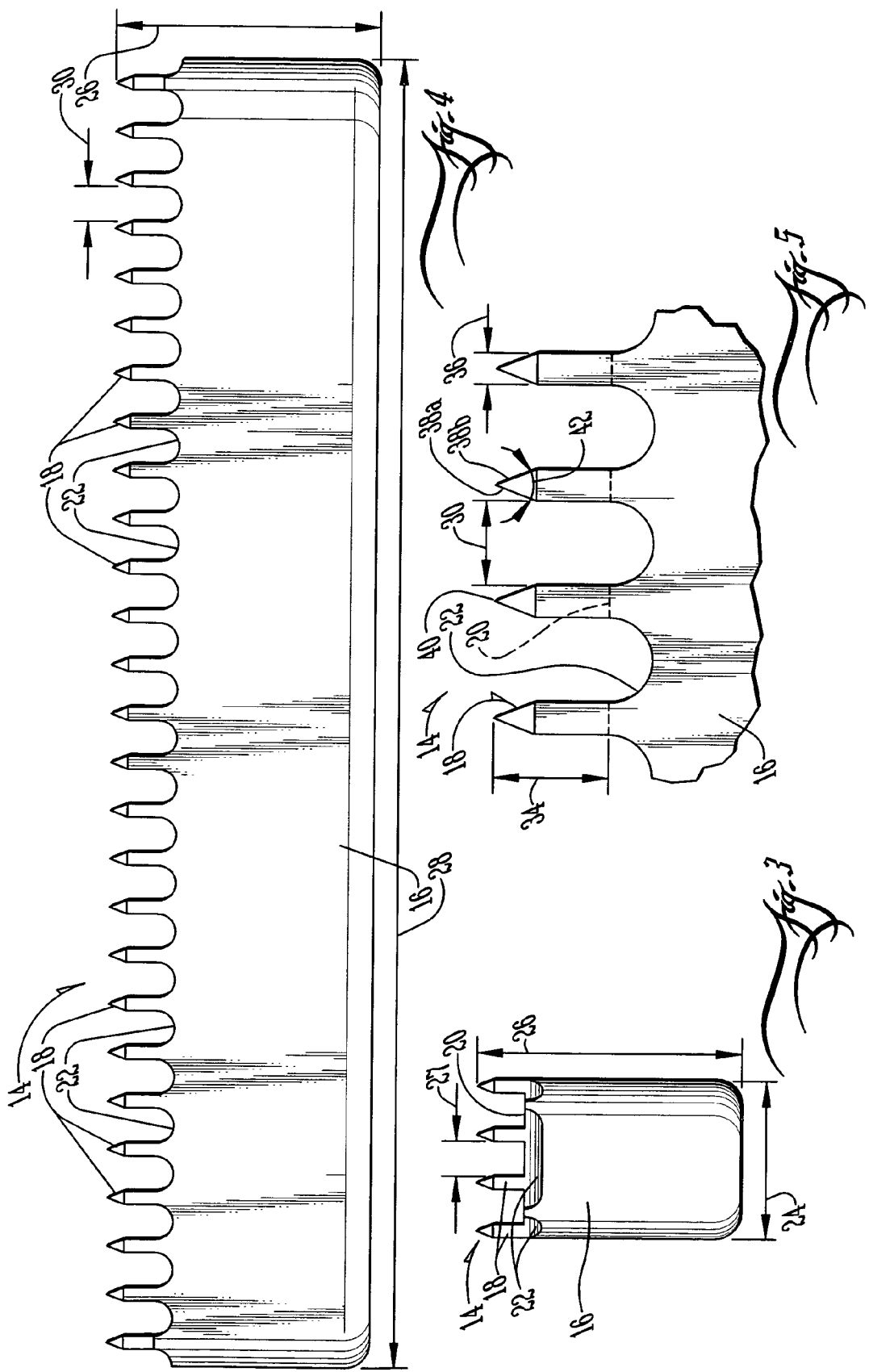

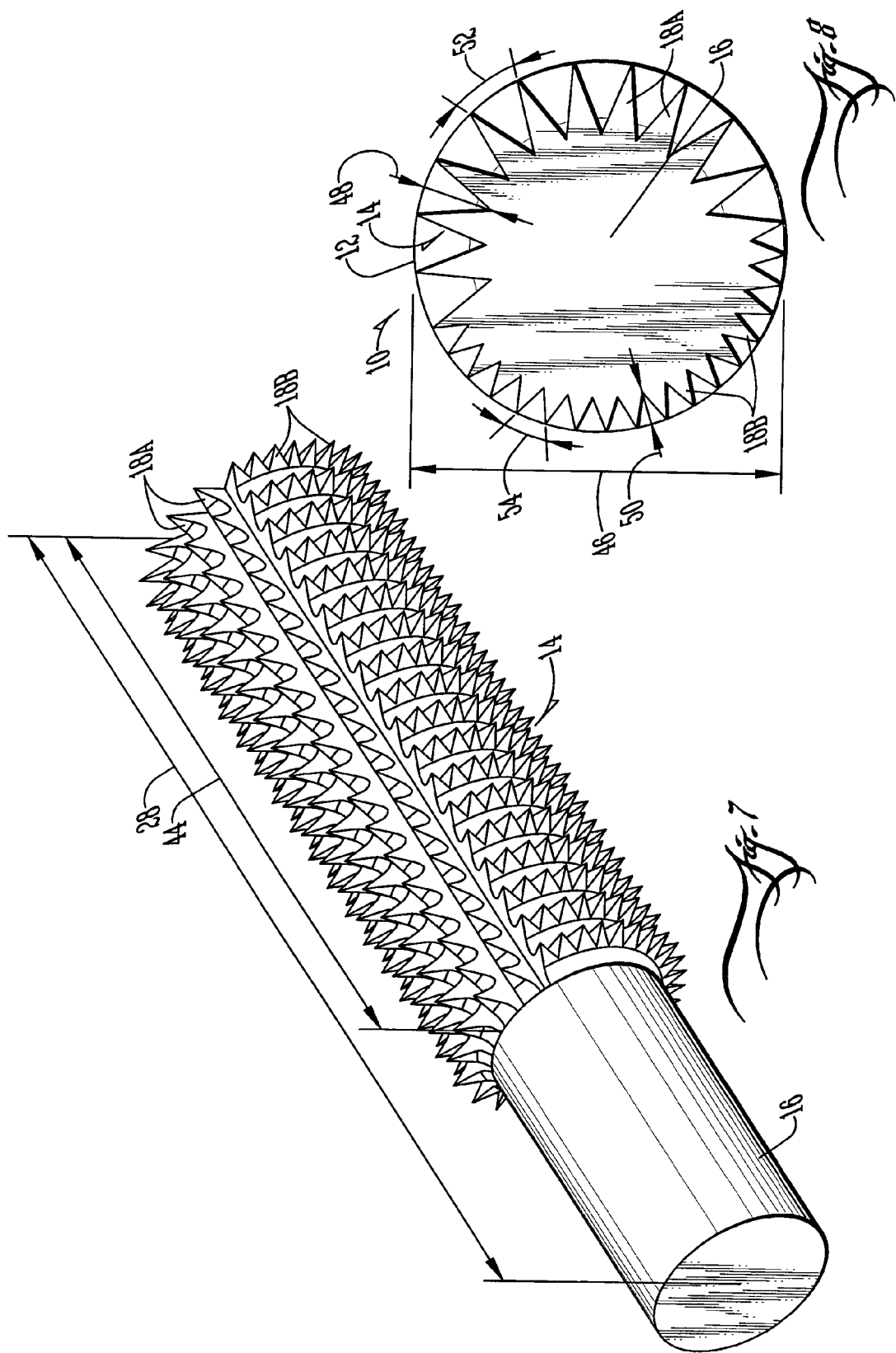

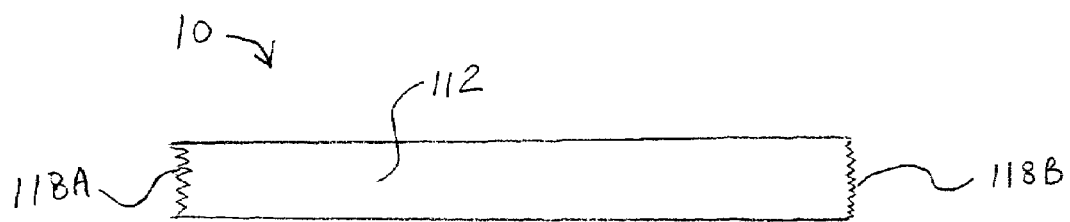
FIG. 9
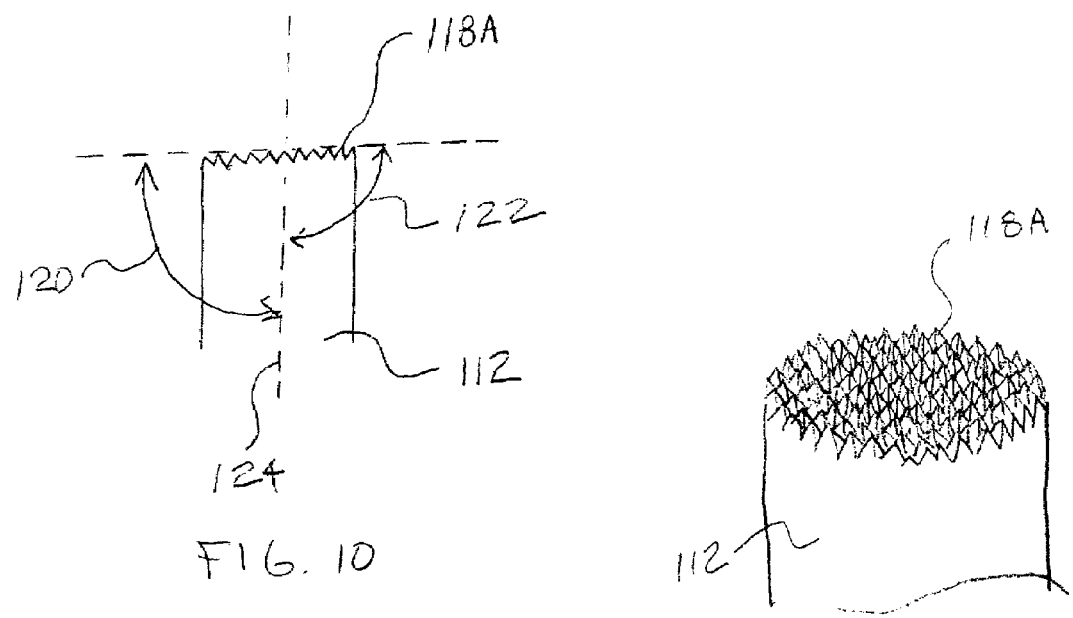
FIG. 10
FIG. 11

WART REMOVAL METHOD AND DEVICE

This application claims priority from and is a continuation-in-part of U.S. patent application Ser. No. 09/851,477, filed on May 8, 2001 now U.S. Pat. No. 6,585,742.

BACKGROUND OF THE INVENTION

This invention relates to wart removal, and more particularly to a method and device for accomplishing wart removal.

A wart is a papillomatous growth characterized by a relatively thick, tough, keratinous outer layer. It is believed that a virus causes warts. A wide variety of wart removal techniques are known in the art. Wart removal techniques include burning and freezing. These techniques must typically be performed by a physician in a clinical setting. Various lotions and medicaments have been developed for topical application. Still, it is difficult to identify a lotion or medicament that is safe for a patient to use at home and that is still able to penetrate the relatively thick, tough, keratinous outer layer of a wart. Physicians have used scalpels and razors to remove warts by cutting or paring. A variety of tools or devices have also been proposed that use roughened surfaces to remove wart tissue over a period of days or weeks by rubbing or abrading. Cutting or paring a wart with a scalpel or razor generally provides superior results as compared to rubbing or abrading a wart with a roughened surface. Still, it is inconvenient and costly for a patient to make repeated trips to a physician for frequent cutting or paring treatments. For obvious safety reasons, physicians and patients are reluctant to have the patient use a scalpel or razor for repeated cutting and paring at home. Nonetheless, using a roughened surface to slowly rub or abrade wart tissue leaves much to be desired. For example, the roughened surfaces typically lack the cutting depth and sharpness to effectively penetrate the stratum corneum, the relatively thick, tough, keratinous outer layer of a wart.

SUMMARY OF THE INVENTION

It is therefore an object of the present invention to provide a wart removal method and device that allows a patient to safely and effectively remove wart tissue.

It is a further object of the present invention to provide a wart removal method and device of the above type that combines the advantages of clinical cutting or paring devices with the convenience of home treatment devices.

It is a still further object of the present invention to provide a method and device of the above type that allows a patient to safely cut away wart tissue without extensive training and without causing noticeable bleeding.

It is a still further object of the present invention to provide a method and device of the above type that allows a patient to safely cut away wart tissue in a specific, pinpointed location.

It is a still further object of the present invention to provide a method and device of the above type that allows a patient to safely use a kit to remove a wart in a non-clinical setting.

It is a still further object of the present invention to provide a device of the above type, and a method of using the same, that provides sufficient cutting depth and sharpness to penetrate the stratum corneum, the relatively thick, tough, keratinous outer layer of a wart and that is still safe for a patient to use in a non-clinical setting.

It is a still further object of the present invention to provide a method and device of the above type that increases the effectiveness of a medicament by allowing a patient to make incisions through the relatively thick, toughened, keratinous outer layer of a wart prior to applying the medicament in a non-clinical setting.

It is a still further object of the present invention to provide a method and device that allows a patient the flexibility to make incisions of different depths as desired.

It is a still further object of the present invention to provide a method and device that allows a patient to make more aggressive, deeper incisions during initial treatments and to make less aggressive, more shallow incisions after initial treatments.

It is a still further object of the present invention to provide a method and device that allows a patient to select between more aggressive and less aggressive treatments based upon levels of comfort or discomfort experienced.

Toward the fulfillment of these and other objects and advantages, a wart removal device and method of using same are disclosed. The device has a handle and first and second pluralities of tines having different heights. One set of tines has a height of approximately 0.04 inch, and the other set has a height of approximately 0.08 inch. The different tine sets may be disposed on opposite sides of the handle at the same end of the handle or may be disposed on opposite ends of the handle. In operation, the longer set of tines is raked against wart tissue to create a plurality of incisions in the wart tissue. This treatment is repeated over a time period. After that time period, the shorter set of tines is used. The tines are designed to create incisions without causing noticeable bleeding. The device may be used in combination with a medicament and may be provided as a kit, including the device and a medicament.

BRIEF DESCRIPTION OF THE DRAWINGS

The above brief description, as well as further objects, features and advantages of the present invention will be more fully appreciated by reference to the following detailed description of the presently preferred but nonetheless illustrative embodiments in accordance with the present invention when taken in conjunction with the accompanying drawings, wherein:

FIG. 1 is a perspective view of a device of the present invention;

FIG. 2 is an enlarged, elevation view of a pad of the present invention;

FIG. 3 is an enlarged, front elevation view of a pad of the present invention;

FIG. 4 is an enlarged, side elevation view of a pad of the present invention;

FIG. 5 is an enlarged sectional view of tines of the present invention;

FIG. 7 is a perspective view of an alternate embodiment of a pad of the present invention;

FIG. 8 is an end view of the alternate embodiment of FIG. 6;

FIG. 9 is an enlarged side view of a second alternate embodiment of the present invention;

FIG. 10 is an enlarged, perspective view of an end portion of the second alternate embodiment and FIG. 11 is an enlarged side view of an end portion of the second alternate embodiment.

DETAILED DESCRIPTION OF THE PREFERRED EMBODIMENT

Figure 6:
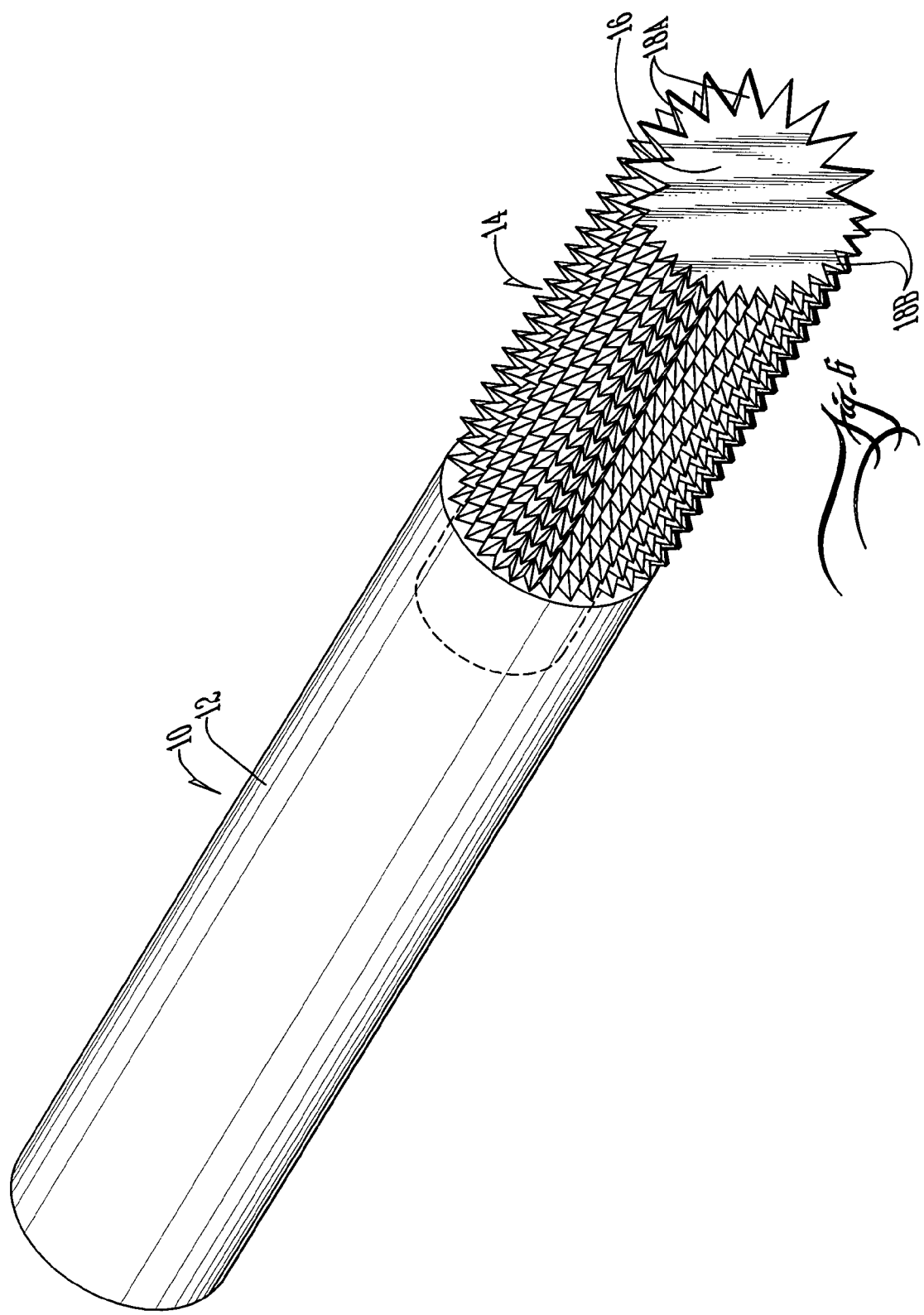
FIG. 6 is a perspective view of an alternate embodiment of the present invention.

Referring to FIG. 1, the reference numeral 10 refers in general to a wart removal device of the present invention. The device 10 comprises a handle 12 and a pad 14. The pad 14 comprises a base 16 and a plurality of tines 18.

The handle 12 is an elongate handle designed to be grasped by a user at a proximal end and having the pad 14 affixed to a distal end. The handle 12 is preferably plastic but may be made from any number of materials. It is preferred that the handle 12 be sufficiently rigid to allow it to hold the pad 14 in place during use. It is of course understood that the pad 14 may take any number of shapes, sizes, or configurations and that the handle 12 may be made from the same material as or formed integrally with the pad 14.

As best seen in FIG. 2, the pad 14 comprises a base 16 and a plurality of tines 18. The pad 14 is affixed to the handle 12 such as by using adhesives or by forming the pad into or as part of the handle. The tines 18 extend upward from the base 16 and are arranged to form a plurality of columns and a plurality of rows. The number of rows is preferably not less than approximately twice the number of columns and is more preferably not less than approximately four times the number of columns. The number of rows is preferably not less than 12, and the number of columns is preferably not greater than 6. In the preferred embodiment shown, the pad 14 has four columns of tines 18 and 27 rows of tines 18. The base 16 preferably provides substantially planar surfaces or ridges 20 that extend between the tines 18 in each row. Curved channels or troughs 22 may be formed in the base 16 between adjacent rows of tines 18. The pad 14 is preferably made from stainless steel but may be made from any number of materials.

As best seen in FIG. 3, the pad 14 has a width 24 that is preferably not greater than approximately ¼ inch, that is more preferably not greater than approximately ⅛ inch, and that is most preferably approximately 0.12 inch. The pad 14 has a height 26 that is preferably not greater than approximately ½ inch, that is more preferably not greater than approximately ¼ inch, and that is most preferably approximately 0.195 inch. Each column of tines 18 is preferably spaced from adjacent columns of tines. The spacing 27 between adjacent columns is preferably, approximately 0.028 inch. As best seen in FIG. 4, the pad 14 has a length 28 that is preferably not less than approximately twice the pad width 24, that is more preferably not less than ½ inch, and that is most preferably approximately 0.95 inch. As also shown in FIG. 4, each row of tines 18 is preferably spaced from adjacent rows of tines 18. The spacing 30 between rows is preferably, approximately 0.026 inch.

As best seen in FIG. 5, each tine 18 has a height 34 and a width 36 that is measured at or near where the tine 18 meets the base 16. The height 34 is preferably greater than the width 36, is more preferably not less than approximately twice the width 36, and is most preferably not less than approximately three times the width 36. The tine height 34 is preferably less than approximately 0.1 inch, is more preferably less than approximately 0.05 inch, and is most preferably approximately 0.034 inch. Each tine 18 is sharpened so that opposing sides 38a and 38b meet to form a point 40 at an upper edge, with the opposing sides forming an angle 42 that is preferably substantially within a range of from approximately 20° to approximately 40°, that is more preferably substantially within a range of from approximately 30° to approximately 40°, and that is most preferably approximately 39°. Each tine 18 is preferably sharpened so that front and rear surfaces of the tine form a point 40 at the upper edge, with the front and rear surfaces forming this angle 42 and so that opposing left and right side surfaces also form a point 40 at the upper edge, with the opposing left and right side surfaces forming this angle 42.

FIGS. 6–8 depict a preferred embodiment of the present invention. As seen in FIG. 6, the pad 14 and base 16 are generally cylindrical and have tines 18A and 18B of different heights. The pad 14 is affixed to the handle 12 such as by using a press fitting, a threaded interface, adhesives, or by forming the pad 14 into or as part of the handle 12. The tines 18A and 18B are disposed around the base 16, extend outward therefrom, and are arranged to form a plurality of columns and rows. A first plurality of tines 18A is disposed in a first area and a second plurality of tines 18B is disposed in a second area. The first and second areas are generally disposed on opposite sides of the pad 14 and base 16, with each area covering a portion of a circumference of the base 16 that is preferably greater than or equal to approximately 90 degrees, that is more preferably greater than or equal to approximately 135 degrees and that is most preferably equal to approximately 180 degrees.

As best seen in FIG. 7, the pad has a length 28 that is preferably less than or equal to approximately 5 inches, that is more preferably less than or equal to approximately 3 inches, and that is most preferably less than or equal to approximately 1.5 inches. The tines 18A and 18B extend along a length of the pad that is preferably less than or equal to approximately 4 inches, that is more preferably less than or equal to approximately 2 inches, and that is most preferably less than or equal to approximately 1 inch. Referring to FIG. 8, the tined portion of the pad has an outer diameter 46, measured from tine points on opposite sides of the pad, that is preferably less than or equal to approximately 1 inch, that is more preferably less than or equal to approximately 0.5 inch, and that is most preferably less than or equal to approximately 0.375 inch.

The tines 18A have a height 48 and tines 18B have a different height 50, with height 48 being greater than height 50. Each tine 18A has a height 48 that is preferably greater than or equal to approximately 0.04 inch, is more preferably greater than or equal to approximately 0.05 inch, and that is most preferably greater than or equal to approximately 0.08 inch. Each tine 18B has a height 50 that is preferably less than or equal to approximately 0.1 inch, is more preferably less than or equal to approximately 0.05 inch, and that is most preferably less than or equal to approximately 0.04 inch. Each tine 18A is sharpened such that opposing faces of adjacent tines 18A form an angle 52 that is preferably less than or equal to approximately 60°, that is more preferably less than or equal to approximately 50°, and that is most preferably less than or equal to approximately 45°. Similarly, each tine 18B is sharpened such that opposing faces of adjacent tines 18B form an angle 54 that is preferably less than or equal to approximately 45°, that is more preferably less than or equal to approximately 35°, and that is most preferably less than or equal to approximately 30°. It is of course understood that more than two sets of tines having different heights, shapes, and sizes may be used and that different tines may be disposed within any particular area. It is also understood that the sets of tines 18A and 18B may be arranged in any number of different manners and configurations on pads of any number of different shapes or sizes.

Another alternate embodiment is depicted in FIGS. 9–11. As seen in FIG. 9, a handle 112 is provided, and sets of tines 118A and 118B are provided on opposite ends of the handle 112.

The handle is preferably an elongate, rigid member that is similar in size to a pencil for easy grasping by a user. The handle has a length that is preferably substantially within a range of from approximately 1 inch to approximately 6 inches, that is more preferably substantially within a range of from approximately 2 inches to approximately 5 inches, and that is most preferably substantially within a range of from approximately 3 inches to approximately 4 inches. Each end has a diameter that is preferably substantially within a range of from approximately 1/8 inch to approximately 1/2 inches, that is more preferably substantially within a range of from approximately 3/16 inch to approximately 3/8 inch, and that is most preferably approximately 1/4 inch.

The tines 118A have a height and tines 118B have a different height, with the height of tines 118A being greater than the height of tines 118B. Each tine 118A has a height that is preferably greater than or equal to approximately 0.03 inch, is more preferably greater than or equal to approximately 0.04 inch, and that is most preferably greater than or equal to approximately 0.05 inch. Each tine 118B has a height that is preferably less than or equal to approximately 0.05 inch, is more preferably less than or equal to approximately 0.04 inch, and that is most preferably less than or equal to approximately 0.025 inch. Each tine 118A is sharpened such that opposing faces of adjacent tines 118A form an angle that is preferably less than or equal to approximately 60°, that is more preferably less than or equal to approximately 50°, and that is most preferably less than or equal to approximately 45°. Similarly, each tine 118B is sharpened such that opposing faces of adjacent tines 118B form an angle that is preferably less than or equal to approximately 60°, that is more preferably less than or equal to approximately 50°, and that is most preferably less than or equal to approximately 45°. It is of course understood that more than two sets of tines having different heights, shapes, and sizes may be used and that different tines may be disposed within any particular area. It is also understood that the sets of tines 118A and 118B may be arranged in any number of different manners and configurations on pads of any number of different shapes or sizes.

The tines 118A and 118B are aligned in a plurality of columns and rows on the ends of the handle 112. As seen in FIG. 11, a plane touching the tips of tines 118A forms two angles 120 and 122 with a centerline 124 of the handle 112. The tines 118A are aligned and positioned so that both angles 120 and 122 are preferably greater than or equal to approximately 30° and less than or equal to 150°, are more preferably greater than or equal to approximately 45° and less than or equal to 135°, and are most preferably equal to approximately 90°. Tines 118B are aligned and positioned in similar fashion.

In operation, it is preferred to have a user soak the wart or area to be treated in water for approximately five to ten minutes to soften the keratin. Along this line, a user might be instructed to perform the treatment after bathing. To use the device 10, a user grasps the handle 12 or 112 and rakes the tines 18 or 118 against wart tissue to create a plurality of incisions, small troughs, or grooves in the tissue. The movement is preferably a rapid back and forth movement, similar to the rapid movement of a toothbrush during brushing. The sharpness and cutting depth of the tines 18 and 118 is selected so that the tines create the incisions in the relatively thick, tough, keratinous outer layer of the wart without causing noticeable bleeding. The tines 18 and 118 are preferably sufficiently long and sharp to penetrate the stratum corneum. The width 24 of the pad 14 is selected to allow a user to accurately pinpoint an area to be treated without also creating incisions in unaffected tissue. The width 24 is also sufficiently narrow to allow the device 10 to be used in hard to reach areas. The length 28 of the pad 14 is selected to allow a user to use long, smooth, slow, controlled strokes. The user continues the raking action for a desired period of time, typically a few seconds. The user may treat the affected area on a regular basis until the desired degree of tissue removal is obtained. The device 10 may also be used in combination with lotions or medicaments designed for wart removal to increase the effectiveness of those lotions or medicaments or may be used in combination with other treatment methods. Pyruvic acid is a preferred medicament, but it is understood that any number of lotions or medicaments may be used, including but not limited to salicylic acid, salicylic acid plasters (such as sold under the trademark Mediplast®), salicylic acid impregnated bandages, imiquimod (sold under the trademark Aldara®), 5-fluorouracil cream or solution, interferon, and a wide variety of alpha hydroxy acids and other known wart treatment lotions, medicaments, and compositions, such as those identified in U.S. Pat. No. 4,363,815, Yu et al., the disclosure of which is incorporated herein by reference. In that regard, a user would rake the device 10 on the affected area to create a plurality of incisions and would then apply the medicament to the affected area.

Creating incisions in the relatively thick, tough, keratinous tissue provides for better contact between the medicament and the tissue to be treated. This is particularly true if the incisions are deep enough to penetrate the stratum corneum.

In the preferred embodiment, depicted in FIGS. 6–8, the user would first use tines 18A for a desired period of time to create deeper incisions and more tissue removal. After one or more uses of the tines 18A having the greater height 48, the user would then use tines 18B having lesser height 50 for a desired period of time. As discussed above, the device could be used in combination with medicaments and other treatments. Providing sets of tines having different heights or cutting characteristics gives a user greater flexibility in deciding how to treat an affected area. For example, the tines 18A of greater height 48 will typically be used initially to provide for more aggressive treatment. After a desired degree of tissue removal is obtained, or after a level of discomfort rises to an undesirable level from using the more aggressive tines 18A, the user may switch to the less aggressive tines 18B having a lesser height 50.

In the alternate embodiment, depicted in FIGS. 9–11, the user would first use tines 118A for a desired period of time to create deeper incisions and more tissue removal. After one or more uses of the tines 118A having the greater height, the user would then use tines 118B having lesser height for a desired period of time. As discussed above, the device could be used in combination with medicaments and other treatments. Providing sets of tines having different heights or cutting characteristics gives a user greater flexibility in deciding how to treat an affected area. For example, the tines 118A of greater height will typically be used initially to provide for more aggressive treatment. After a desired degree of tissue removal is obtained, or after a level of discomfort rises to an undesirable level from using the more aggressive tines 118A, the user may switch to the less aggressive tines 118B having a lesser height.

The device 10 is best suited for use in connection with thick warts located on the palms of the hands, soles of the feet, and around toenails and fingernails. It is of course understood that the device may be used to treat warts in other areas or to treat other conditions.

The device 10 and medicament may be sold together as a kit. In the past, physicians and patients have been understandably reluctant to have the patient perform self-treatment using a sharp cutting device. The present device makes self-treatment much more safe and practical. Still, the kit would preferably be sold by prescription only so that a physician could provide some counseling or training on proper techniques for using the device 10. Similarly, if sold by prescription only, the counseling or training offered by the physician would make it safer to provide a stronger, more concentrated medicament to the patient to further increase the effectiveness of the treatments.

Other modifications, changes, and substitutions are intended in the foregoing, and in some instances, some features of the invention will be employed without a corresponding use of other features. For example, the sloping surfaces 38a and 38b forming the point 40 at the upper edge of each tine 18 may extend over all or substantially all of the height 34 of the tine 18. Similarly, the tines 18 may be formed separately from or formed integrally with the base 16. The device 10 may also be used with or without an accompanying use of medicament. Further still, although the device 10 has been described as being used in connection with wart removal in a non-clinical setting, the device 10 may be used by physicians in a clinical setting and may be used to remove tissue other than wart tissue. It is understood that all measurements and quantitative information are given by way of example only and are not intended to limit the scope of the invention. Accordingly, it is appropriate that the appended claims be construed broadly and in a manner consistent with the scope of the invention.

What is claimed is:

1. A method of treating wart tissue, comprising: (1) providing a pad, comprising a first plurality of tines having a first height disposed in a first area, and a second plurality of tines having a second height disposed in a second area, said first height being different from said second height; and (2) raking said first plurality of tines against wart tissue to create a first plurality of incisions in said tissue.

2. The method of claim 1, further comprising, after step (2), raking said second plurality of tines against said wart tissue to create a second plurality of incisions in said tissue.

3. The method of claim 1, wherein step (1) comprises providing said pad, comprising said first plurality of tines having said first height disposed in said first area, and said second plurality of tines having said second height disposed in said second area, said first height being greater than said second height.

4. The method of claim 3, further comprising, after step (2), raking said second plurality of tines against said wart tissue to create a second plurality of incisions in said tissue.

5. The method of claim 1, further comprising, after step (2), applying a medicament to said wart tissue.

6. The method of claim 1, further comprising, after step (2), applying pyruvic acid to said wart tissue.

7. The method of claim 1, further comprising, repeating step (2) for a desired number of repetitions executed periodically over a first time period.

8. The method of claim 7, further comprising, after said first time period, raking said second plurality of tines against said wart tissue to create a second plurality of incisions in said tissue.

9. A kit for treating warts, comprising: a medicament; and a device, said device comprising: a handle; and a first plurality of tines affixed to said handle and being disposed in a first area, said first plurality of tines having a first height; and a second plurality of tines affixed to said handle and being disposed in a second area, said second plurality of tines having a second height that is greater than said first height.

10. The kit of claim 9, wherein said first height is less than or equal to approximately 0.1 inch.

11. The kit of claim 9, wherein said second height is greater than or equal to approximately 0.05 inch.

12. The kit of claim 9, wherein said medicament comprises pyruvic acid.

* * * * *